(12) United States Patent
Spry et al.

(10) Patent No.: US 9,739,736 B2
(45) Date of Patent: Aug. 22, 2017

(54) HF ALKYLATION PROCESS

(71) Applicants: David Benjamin Spry, Baton Rouge, LA (US); Jeffrey M. Fitt, Centreville, VA (US)

(72) Inventors: David Benjamin Spry, Baton Rouge, LA (US); Jeffrey M. Fitt, Centreville, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 149 days.

(21) Appl. No.: 14/556,389

(22) Filed: Dec. 1, 2014

(65) Prior Publication Data

US 2015/0198550 A1    Jul. 16, 2015

Related U.S. Application Data

(60) Provisional application No. 61/917,972, filed on Dec. 19, 2013.

(51) Int. Cl.
| | |
|---|---|
| *G01N 27/06* | (2006.01) |
| *C07C 2/62* | (2006.01) |
| *C10G 29/20* | (2006.01) |
| *B01J 19/24* | (2006.01) |
| *G01N 25/00* | (2006.01) |
| *G01N 9/36* | (2006.01) |

(52) U.S. Cl.
CPC .............. *G01N 27/06* (2013.01); *B01J 19/24* (2013.01); *C07C 2/62* (2013.01); *C10G 29/205* (2013.01); *G01N 25/00* (2013.01); *B01J 2219/24* (2013.01); *C07C 2527/1206* (2013.01); *G01N 9/36* (2013.01)

(58) Field of Classification Search
CPC ........................... G01N 27/06; G01N 2440/12
USPC ........................................................ 73/61.44
See application file for complete search history.

(56) References Cited

U.S. PATENT DOCUMENTS

| | | | |
|---|---|---|---|
| 2,850,552 A | 9/1958 | Olgle | |
| 3,293,320 A | 12/1966 | Magearl et al. | |
| 3,668,392 A * | 6/1972 | Bajek ..................... | G01N 23/10 |
| | | | 378/52 |
| 5,707,923 A | 1/1998 | Hutchens et al. | |
| 6,096,553 A | 8/2000 | Heald et al. | |

(Continued)

OTHER PUBLICATIONS

PCT Application No. PCT/US2014/068259, Communication from the International Seaching Authority, Form PCT/ISA/220, dated Feb. 24, 2014, 10 pages, Aug. 31, 2016.

*Primary Examiner* — David Gray
*Assistant Examiner* — Andrew V Do
(74) *Attorney, Agent, or Firm* — Andrew T. Ward

(57) ABSTRACT

An HF olefin/isoparaffin alkylation process is carried out in an alkylation unit with a settling vessel in which the alkylate product is separated from the HF acid catalyst containing water and acid soluble oil (ASO). The density of the liquids in the settling vessel is measured at different levels by means of a nuclear density profile analyzer. The acid strength of the acid phase is determined from the density measurement and an optional temperature measurement. The proportion of water in the acid phase may also be measured separately by measurement of its electrical conductivity to determine the respective contributions of the water and the ASO to the density of the HF acid phase.

17 Claims, 1 Drawing Sheet

(56) References Cited

U.S. PATENT DOCUMENTS

| | | | |
|---|---|---|---|
| 6,548,814 B1* | 4/2003 | Gronli | G01N 23/04 |
| | | | 250/357.1 |
| 6,633,625 B2 | 10/2003 | Jackson et al. | |
| 7,972,863 B2 | 7/2011 | Trygstad et al. | |
| 2002/0121371 A1 | 9/2002 | Moake et al. | |
| 2010/0023275 A1* | 1/2010 | Trygstad | G01N 21/359 |
| | | | 702/25 |

* cited by examiner

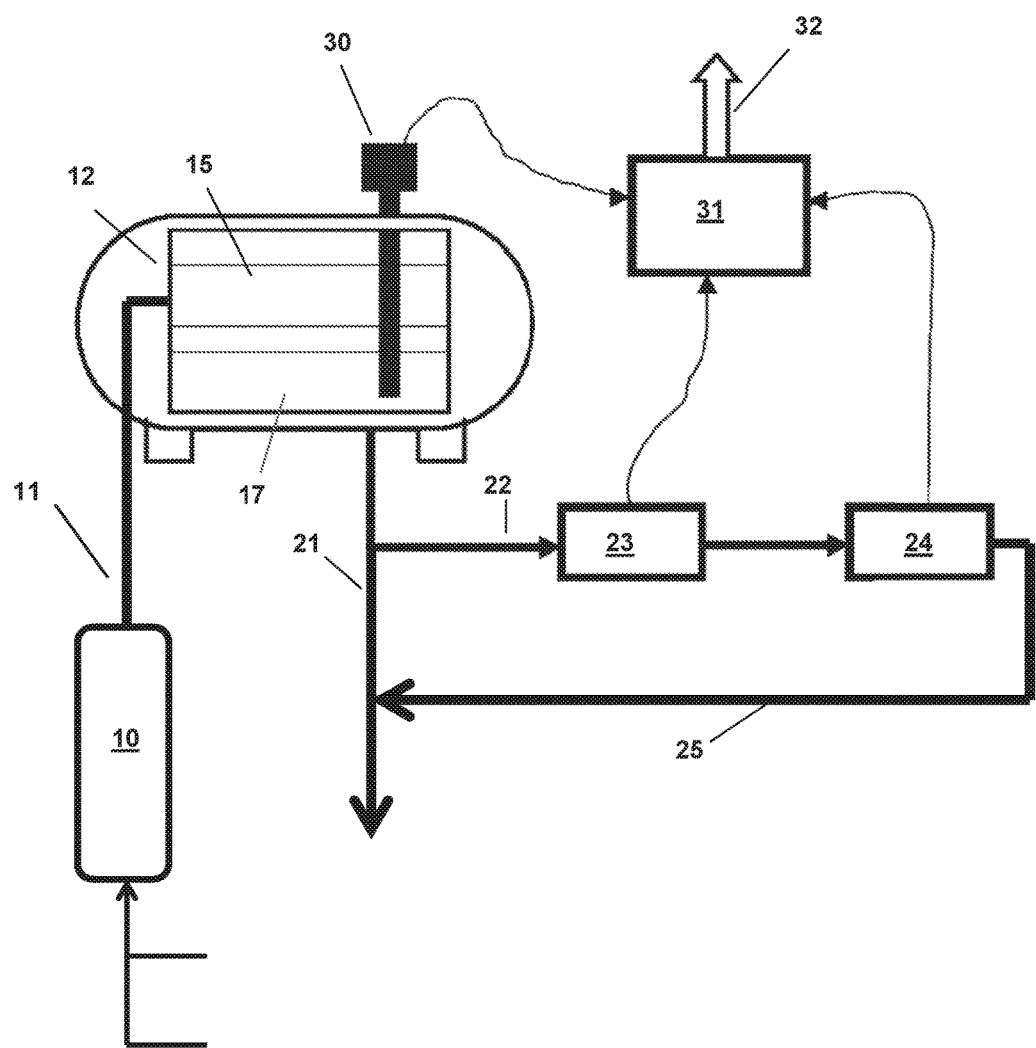

HF ALKYLATION PROCESS

CROSS-REFERENCE TO RELATED APPLICATIONS

This application claims priority to U.S. Provisional Application Ser. No. 61/917,972 filed Dec. 19, 2013, herein incorporated by reference in its entirety.

FIELD OF THE INVENTION

This invention relates to iso-paraffin/olefin alkylation and more particularly, to hydrofluoric acid (HF) alkylation. In this specification, the term "alkylation" will be used to refer to the iso-paraffin/olefin alkylation process used to make gasoline blend components useful in aviation and motor gasolines and "HF alkylation" to this process using hydrofluoric acid as the catalyst.

BACKGROUND OF THE INVENTION

The isoparaffin/olefin alkylation process is widely used to manufacture a high octane quality blend component for aviation and motor gasoline which is also valued for its relatively low vapor pressure, low sensitivity and, because of its freedom from sulfur and aromatic components, its environmental acceptability. The process typically reacts a $C_2$ to $C_5$ olefin with a light ($C_4$ to $C_5$) isoparaffin, typically isobutane, in the presence of an acidic catalyst to produce the alkylate product.

Hydrofluoric and sulfuric acid alkylation processes share inherent drawbacks including environmental and safety concerns, acid consumption, and sludge disposal but in spite of efforts to develop an inherently safe alkylation process, both processes have achieved widespread utilization with the HF process being noted for producing a higher quality product with more favorable unit economics. Although hydrogen fluoride, or hydrofluoric acid (HF) is highly toxic and corrosive, extensive experience in its use in the refinery have shown that it can be handled safely, provided the hazards are recognized and precautions taken. The HF alkylation process is described in general terms in *Modern Petroleum Technology*, Hobson et al (Ed), Applied Science Publishers Ltd. 1973, ISBN 085334 487 6. A survey of HE alkylation may be found in *Handbook of Petroleum Refining Processes*, Meyers, R. A. (Ed.). McGraw-Hill Professional Publishing, 2nd edition (Aug. 1, 1996), ISBN: 0070417962.

Monitoring acid strength is necessary to optimize alkylation product, reduce operating expenses, and prevent unit upsets. Acid strength effects the yield and octane number (quality) of the alkylate product. Low acid strength levels result in so-called acid runaway, where olefin polymerization is favored over the desired alkylation reaction, which further lowers the acid strength with the addition of the by-product polymer (acid soluble oil, ASO) to the mixture and leads to a positive feedback cycle rapidly consuming the acid catalyst and producing polymer sludge and reaction intermediates. A common result of acid runaway is unit shutdown.

A similar problem of making on-line measurement of acid strength is found in sulfuric acid alkylation units, where sulfuric acid strength measurements are also required for optimal operation. With the high relative density of sulfuric acid (1.84) relative to water and ASO (1 and ~0.7-0.9, respectively), which are the two other primary components in the system, it is common to use density to quantify sulfuric acid strength. U.S. Pat. No. 5,707,923 (Hutchens) discloses the use of density measurements on the reaction mixture for the determination of operating limits including acid strength. Because the density differences in HF units are not as great as with sulfuric acid, density measurement is not commonly used to measure HF acid strength; in addition, material incompatibilities between many metals commonly found in densitometers and HF preclude its use in any extensive practice.

U.S. Pat. No. 7,972,863 (Trygstad) discloses a method for determining the concentration of components in the liquid mixture flowing through the alkylation process by measuring certain properties of the mixture which are independent of the concentration of the water in the mixture; the temperature of the mixture is also measured to enable a temperature compensated concentration to be determined.

Another technology for on-line acid strength measurement is marketed by K-Patents Oy (Finland) and is based upon refractive index measurements. The company has sold the product for sulfuric acid strength measurements but so far, refractive index measurements have not been successfully implemented in a commercial setting for measuring HF acid strength even though the refractive index of HF (1.15) is much lower than water (1.33) or ASO (1.4), which in principle could allow changes in acid strength to be inferred from changes in refractive index. Material incompatibilities with HF have, however, been a negative factor to utilizing the technique in HF alkylation units.

Currently, acid strength measurements in HF alkylation units are most commonly made by manual sampling and laboratory analysis. The analysis is time consuming and typically performed at most once per day; more commonly it is performed only hi-weekly or even weekly. At such low analysis frequencies, it is difficult to monitor rapidly changing process conditions. Manual analysis presents a legitimate safety risk. Hydrofluoric acid is highly toxic and extremely volatile. Contact with the skin causes severe burns and is readily absorbed into the body, where it reacts with calcium causing bone damage and possibly cardiac arrest. Inhaling gaseous hydrofluoric acid can cause irreversible lung damage at concentrations over 10 ppm.

The only commercially-implemented automated analysis technique used to quantify HF acid strength uses Infrared (IR) Spectroscopy. IR Spectroscopy is a relatively complicated technique that is difficult and costly to implement in an alkylation unit. The IR system requires an automated sample conditioning system, which has many moving parts and possible leak sources. To mitigate the possibility of a leak involving HF, the IR system has integrated HF detectors that are tied into an automated shutdown system that closes sample supply and evacuates the system with nitrogen. In addition IR spectroscopy is maintenance intensive and requires an air-conditioned, vibration-free environment. Typical cost of an IR system including installation is more than $2 M USD.

SUMMARY OF THE INVENTION

The present invention makes use of existing equipment, as in HF alkylation plants that already use a density profile analyzer to monitor the position of the liquid interface between the alkylate product and the HF acid phase in the acid settler used to separate the alkylate from the denser HF acid phase. According to the present invention, the density profiler is also utilized to determine the acid strength from the density of the acid phase. Making use of the density data, which is acquired in the process of making the measurement of the position of the alkylate/acid interface can reduce the cost of an on-line acid strength measurement by a significant factor. While the installation of an additional instrument in the process line would add possible failure or leak points, the present invention makes dual use of equipment, which decreases both equipment cost and the risk of a loss of containment from additional process connections.

According to the present invention, the HF acid strength of the acid in an HF olefin/iso-paraffin alkylation unit in which a $C_2$ to $C_5$ olefin is reacted with a $C_4$-$C_5$ isoparaffin is determined by measuring the density in the HF acid phase in the settler by means of a density profile analyzer and correlating the measured density to acid strength. The proportion of water in the layer may also be measured separately by measurement of electrical conductivity and its temperature may likewise be monitored by a temperature sensor and the measured conductivity and temperature used to correlate with the density determination.

The unit in which the alkylation is carried out comprises: a reactor in which the olefin stream is reacted with the isoparaffin stream to form the alkylate product of higher molecular weight branched chain paraffins; a settling vessel in which the reaction product is separated into a liquid alkylate phase and a denser liquid HF acid phase containing acid soluble oil (ASO); a density profiler for measuring the density of the liquid phases at vertically spaced intervals in the settling vessel, means for determining the density of the HF acid phase from the density profile measured by the density profiler to determine the acid strength of the HF acid phase.

In addition, the unit will usually include a water concentration detector and a temperature sensor to enable the measured density to be adjusted for the relative contributions of the water and the ASO and for a temperature correction to be applied.

DRAWINGS

The single FIGURE of the accompanying drawings is a simplified diagram of a settler vessel of an HF alkylation unit with a nuclear density profiler for monitoring the depths of the layers in the vessel.

DETAILED DESCRIPTION

In recent years, nuclear density profile analyzers have become widely used commercially in the petroleum refining industry to measure the acid height in the settler vessel. The profile analyzer scans the vertical density profile in the settling tank and identifies the boundary between the light hydrocarbon(alkylate) phase and a denser acid phase. The three primary components of the acid phase are HF acid, water, and acid soluble oil (ASO) but because these components differ in density and, in addition, the density of the ASO may vary in a manner which is not predictable, the density measurement on the acid phase cannot directly determine the concentration of the acid relative to the ASO. In addition, water-HF mixtures are very non-ideal and the density of the mixture is significantly higher than the individual components.

In the FIGURE, a nuclear density profile analyzer simultaneously measures the height of the acid phase in the acid settling tank and the position of the interface between the alkylate and the acid phase and in addition, obtains an indication of the HF acid strength by measuring the density of the HF acid phase which is dependent on the concentration of water and ASO in the acid phase. In the unit, the olefin/isoparaffin feed HC and the HF alkylation catalyst meet in reactor 10 and then pass through line 11 to settling tank 12 were the alkylate product phase and the denser HF acid phase are allowed to separate in the usual way under gravity with a supernatant alkylate phase and a denser acid phase. The alkylate phase 15 forms the least dense layer while the denser HF acid phase 17 accumulates in the lower portion of the settler. The HF acid/water stream is withdrawn through line 21 with its inlet in the lower portion of the settler and passes to the acid recovery unit in the usual manner. A slip stream is withdrawn from line 21 and passes through recirculation line 22 to conductivity meter 23 and an optional temperature measurement module 24 before being returned to line 21 by way of line 25, so providing for a continuously updated indication of the conductivity and optionally, the temperature of the acid phase in the settler.

A nuclear density profile analyzer 30 is shown extending into the tank, e.g. in a dry well although an externally mounted profile analyzer may also be used. If the internal drywell type analyzer is used, the detectors may be mounted on the exterior of the vessel at various selected heights or a single detector may be scanned with the source in a separate drywell; if the density is measured at various depths where the acid/hydrocarbon interface is to be found, e.g. with more than one detector at the expected depth of the interface, the average density of the acid phase in the region may be used for the density determination. Typically, the density of the acid phase is measured at or just below the hydrocarbon/acid interface. The outputs from the conductivity meter 23, the temperature module 24 and the densitometer 30 are passed to a monitoring/control module 31 where the density and conductivity measurements are convolved together with the temperature measurement, if taken. The output representing the HF acid strength may then be read out through line 32.

One type of nuclear density profiler is described in U.S. Pat. No. 6,633,625 (Jackson/Johnson Matthey) using collimated ionizing radiation beams with an axially distributed radiation detector array in which each detector is associated with one of the beams to produce an output signal in response to incident radiation. In a typical commercial density profiler a dip pipe extending into the vessel through a flange holds an array of low-energy gamma sources with a collimator with holes at each source level. These holes direct a narrow beam of radiation toward a selected detector so that each source is matched to the radiation source in the same plane. The liquid between the dip pipes will attenuate the radiation with the intensity of the detected radiation proportional to the density of the intervening liquid, this providing an output signal indicative of the liquid density at each source/detector plane. The outputs from the detectors are transmitted for analysis, for instance, by wire or fiber-optic link to a programmable logic controller that collects the information and calculates the density profile.

Various nuclear density profilers are commercially available such as the Nitus™ system from Thermo Fisher Scientific, the Tracerco™ Profiler from Johnson Matthey, the Delta Controls IPT (Interface Position Transmitter) and the Ohmart Vega MDA FiberFlex® interface profiler as well as the Profile Vision device from Endress+Hauser. The profiler typically operates from an internal drywell with multi-level radiation sources with internal or external detectors for each interface level. The type with internal drywell detectors has the advantage of easy installation while the external detectors are less sensitive to temperature and do not require temperature control to preserve system integrity but since the acid density varies with temperature, a correlation with liquid temperature to provide a temperature correction is nevertheless desirable.

The HF acid strength may then be determined from the measurements according to the following methodology:

Assuming variations in concentration and temperature are relatively small, the density is a linear function of all of the components and temperature:

$$\rho = \alpha \cdot c_{HF} + \beta \cdot c_{H_2O} + \gamma \cdot T + \delta \quad (1)$$

where $\rho$ is the measured density of the acid phase in the settler, $c_{HF}$ and $c_{H_2O}$ are HF and water concentration, T is measured temperature, and $\alpha$, $\beta$, $\gamma$, and $\delta$ are fitting parameters. The terms $\alpha$ and $\beta$ represent the densities of HIP and water and the term $\gamma$ accounts for the temperature-dependent solubility of hydrocarbon and also the temperature effects on density. The liquid density is also dependent on the ASO concentration but since $c_{HF} + c_{H_2O} + c_{ASO} = 1$, the equation is simplified and reduced to a system of three unknowns with one constraint (components adding to unity) and two measurements (density and conductivity), so permitting a solution in which the acid strength is expressed as directly dependent on the water the density and water concentration.

$$c_{HF} = A \cdot \rho + B \cdot c_{H_2O} + C \cdot T + D \quad (2)$$

where, in this case, the fitting parameters are A, B C and D. Additional measurements, including the water concentration from the conductivity measurement and the temperature correction can be included in a model, which calculates the acid strength resulting from the various input variables.

ADDITIONAL EMBODIMENTS

Embodiment 1

In a method of determining the HF acid strength of the HF acid in an HF olefin/iso-paraffin alkylation unit having a settling vessel in which a hydrocarbon phase comprising alkylate and an HF acid phase containing acid soluble oil (ASO) and water are separated into a hydrocarbon phase and a denser HF acid phase with an interface between the two phases, the method comprising determining the density of the HF acid phase from the density profile of the hydrocarbon and HF acid phases in the settling vessel and from the density of the HF acid phase determining the proportion of water and ASO in the HF acid phase to determine the HF acid strength.

Embodiment 2

In an olefin/isoparaffin HF alkylation process in which a $C_2$ to $C_5$ olefin is reacted with a $C_3$-$C_6$ isoparaffin in the presence of an HF acid catalyst to form a higher molecular weight alkylate reaction product comprising branched chain paraffins which is separated from an HF acid phase containing water and acid soluble oil (ASO) in a settling vessel, the method of determining the HF acid strength of the HF acid in the settling vessel by determining the density of the HF acid phase from the density profile of the hydrocarbon and HF acid phases in the settling vessel and from the density of the HF acid phase and determining the proportion of water and ASO in the HF acid phase to determine the HF acid strength.

Embodiment 3

A method according to Embodiment 1 or Embodiment 2 in which the density of the HF acid phase is measured by means of a nuclear density profiler.

Embodiment 4

A method according to anyone of the previous Embodiments in which the proportion of water in the HF acid phase is determined by means of a measurement of electrical conductivity.

Embodiment 5

A method according to anyone of the previous Embodiments in which the temperature of the HF acid phase is measured.

Embodiment 6

A method according to anyone of the previous Embodiments in which the density of the HF acid phase is determined at or below the interface between the hydrocarbon phase and the HF acid phase.

Embodiment 7

A method according to anyone of the previous Embodiments in which the HF acid strength is determined from measurements of the density of the HF acid phase, of the temperature and the proportion of water in the acid phase and the IV acid strength is determined from the measured density, temperature and water proportion of the HF acid phase according to the relationship:

$$c_{HF} = A \cdot \rho + B \cdot c_{H_2O} + C \cdot T + D$$

where $c_{HF}$ and $c_{H_2O}$ are respectively, the HF and water concentration, $\rho$ is the measured density, T is the measured temperature, and A, B, C, D are fitting parameters.

Embodiment 8

An HF olefin/iso-paraffin alkylation unit comprising: a reactor in which a $C_2$ to $C_5$ olefin is reacted with a $C_4$-$C_5$ isoparaffin to form a higher molecular weight alkylate reaction product comprising branched chain paraffins; a settling vessel in which the reaction product is separated into a liquid hydrocarbon phase and a denser liquid HF acid phase containing acid soluble oil (ASO); a density profiler for measuring the density of the liquid phases at vertically spaced intervals in the settling vessel, means for determining the density of the HF acid phase from the density profile measured by the nuclear density profiler to determine the acid strength of the IV acid phase.

Embodiment 9

An alkylation unit according to Embodiment 8 which includes an electrical conductivity meter for measuring the electrical conductivity of the HF acid phase.

Embodiment 10

An alkylation unit according to any one of Embodiments 8 and 9 which includes a temperature sensor for measuring the temperature of the acid phase.

Embodiment 11

An alkylation unit according to any one of Embodiments 8-10 which includes a recirculation line extending from the lower portion of the settling vessel to an inlet of the reactor with an electrical conductivity meter located along the line for measuring the electrical conductivity of the HF acid phase in the line.

Embodiment 12

An alkylation unit according to any one of Embodiments 8-11 which includes a recirculation line extending from the lower portion of the settling vessel to an inlet of the reactor with a temperature sensor for measuring the temperature of the HF acid phase in the line.

Embodiment 13

An alkylation unit according to any one of Embodiments 8-12 which includes means for determining the density of the HF acid phase at an interface between the hydrocarbon phase and the IV acid phase.

Embodiment 14

An alkylation unit according to any one of Embodiments 8-13 which includes means for determining the HF acid strength from measurements of the density of the HF acid phase, of the temperature and the proportion of water of the HD acid phase and the HF acid strength is determined from the measured density, temperature and water proportion of the HF acid phase according to the relationship:

$$c_{HF}=A\cdot\rho+B\cdot c_{H_2O}+C\cdot T+D$$

where $c_{HF}$ and $c_{H2O}$ are respectively, the HF and water concentration, $\rho$ is the measured density, T is the measured temperature, and A, B, C, D are fitting parameters.

The invention claimed is:

1. In a method of determining the HF acid strength of the HF acid in an HF olefin/iso-paraffin alkylation unit having a settling vessel in which a hydrocarbon phase comprising alkylate and an HF acid phase containing acid soluble oil (ASO) and water are separated into a hydrocarbon phase and a denser HF acid phase with an interface between the two phases, the method comprising determining the density of the HF acid phase from the density profile of the hydrocarbon and HF acid phases in the settling vessel and from the density of the HF acid phase determining the proportion of water and ASO in the HF acid phase to determine the HF acid strength; wherein the HF acid strength is determined from measurements of the density of the HF acid phase, of the temperature and the proportion of water in the acid phase and the HF acid strength is determined from the measured density, temperature and water proportion of the HF acid phase according to the relationship:

$$c_{HF}=A\cdot\rho+B\cdot c_{H_2O}+C\cdot T+D$$

where $c_{HF}$ and $c_{H2O}$ are respectively, the HF and water concentration, $\rho$ is the measured density, T is the measured temperature, and A, B, C, D are fitting parameters.

2. A method according to claim 1 in which the density of the HF acid phase is measured by means of a nuclear density profiler.

3. A method according to claim 1 in which the proportion of water in the HF acid phase is determined by means of a measurement of electrical conductivity.

4. A method according to claim 1 in which the temperature of the HF acid phase is measured.

5. A method according to claim 1 in which the density of the HF acid phase is determined at or below the interface between the hydrocarbon phase and the HF acid phase.

6. A method according to claim 1 in which the water concentration is determined by measurement of the conductivity of the HF acid phase.

7. In an olefin/isoparaffin HF alkylation process in which a $C_2$ to $C_5$ olefin is reacted with a $C_3$-$C_6$ isoparaffin in the presence of an HF acid catalyst to form a higher molecular weight alkylate reaction product comprising branched chain paraffins which is separated from an HF acid phase containing water and acid soluble oil (ASO) in a settling vessel, the method of determining the HF acid strength of the HF acid in the settling vessel by determining the density of the HF acid phase from the density profile of the hydrocarbon and HF acid phases in the settling vessel and from the density of the HF acid phase and determining the proportion of water and ASO in the HF acid phase to determine the HF acid strength; wherein the HF acid strength is determined from measurements of the density of the HF acid phase, of the temperature and the proportion of water in the HF acid phase and the HF acid strength is determined from the measured density, temperature and water proportion of the HF acid phase according to the relationship:

$$c_{HF}=A\cdot\rho+B\cdot c_{H_2O}+C\cdot T+D$$

where $c_{HF}$ and $c_{H2O}$ are respectively, the HF and water concentration, $\rho$ is the measured density, T is the measured temperature, and A, B, C, D are fitting parameters.

8. A method according to claim 7 in which the density of the HF acid phase is measured by means of a nuclear density profiler.

9. A method according to claim 7 in which the proportion of water in the HF acid phase is determined by means of a measurement of electrical conductivity.

10. A method according to claim 7 in which the temperature of the HF acid phase is measured.

11. A method according to claim 7 in which the density of the HF acid phase is determined at or below the interface between the hydrocarbon phase and the HF acid phase.

12. An HF olefin/iso-paraffin alkylation unit comprising:
a reactor in which a $C_2$ to $C_5$ olefin is reacted with a $C_4$-$C_5$ isoparaffin to form a higher molecular weight alkylate reaction product comprising branched chain paraffins;
a settling vessel in which the reaction product is separated into a liquid hydrocarbon phase and a denser liquid HF acid phase containing acid soluble oil (ASO);
a density profiler for measuring the density of the liquid phases at vertically spaced intervals in the settling vessel,
means for determining the density of the HF acid phase from the density profile measured by the nuclear density profiler to determine the acid strength of the HF acid phase: and
means for determining the HF acid strength from measurements of the density of the HF acid phase, of the temperature and the proportion of water of the HD acid phase and the HF acid strength is determined from the measured density, temperature and water proportion of the HF acid phase according to the relationship:

$$c_{HF}=A\cdot\rho+B\cdot c_{H_2O}+C\cdot T+D$$

where $c_{HF}$ and $c_{H2O}$ are respectively, the HF and water concentration, $\rho$ is the measured density, T is the measured temperature, and A, B, C, D are fitting parameters.

13. An alkylation unit according to claim 12 which includes an electrical conductivity meter for measuring the electrical conductivity of the HF acid phase.

14. An alkylation unit according to claim 12 which includes a temperature sensor for measuring the temperature of the HF acid phase.

15. An alkylation unit according to claim 12 which includes a recirculation line extending from the lower portion of the settling vessel to an inlet of the reactor with an electrical conductivity meter located along the line for measuring the electrical conductivity of the HF acid phase in the line.

16. An alkylation unit according to claim 12 which includes a recirculation line extending from the lower portion of the settling vessel to an inlet of the reactor with a temperature sensor for measuring the temperature of the HF acid phase in the line.

17. An alkylation unit according to claim 12 which includes means for determining the density of the HF acid phase at an interface between the hydrocarbon phase and the HF acid phase.

* * * * *